(12) United States Patent
Akhund

(10) Patent No.: US 10,202,313 B2
(45) Date of Patent: Feb. 12, 2019

(54) PLANT SUPPLEMENTS AND RELATED METHODS

(71) Applicant: Natural Organic Technologies, Inc., Visalia, CA (US)

(72) Inventor: Imran Akhund, Visalia, CA (US)

( * ) Notice: Subject to any disclaimer, the term of this patent is extended or adjusted under 35 U.S.C. 154(b) by 18 days.

(21) Appl. No.: 15/482,700

(22) Filed: Apr. 7, 2017

(65) Prior Publication Data

US 2018/0290938 A1   Oct. 11, 2018

(51) Int. Cl.
| | |
|---|---|
| *C05C 5/04* | (2006.01) |
| *C05D 3/00* | (2006.01) |
| *C05D 5/00* | (2006.01) |
| *C05D 9/00* | (2006.01) |
| *C05G 3/00* | (2006.01) |
| *A01N 59/00* | (2006.01) |
| *A01N 59/06* | (2006.01) |
| *C05C 11/00* | (2006.01) |

(52) U.S. Cl.
CPC ............... *C05D 3/00* (2013.01); *A01N 59/06* (2013.01); *C05C 5/04* (2013.01); *C05C 11/00* (2013.01); *C05G 3/00* (2013.01); *C05G 3/007* (2013.01)

(58) Field of Classification Search
CPC .......... A01N 59/00; A01N 59/06; C05D 3/00; C05C 5/04; C05C 11/00; C05G 3/00; C05G 3/0076
See application file for complete search history.

(56) References Cited

U.S. PATENT DOCUMENTS

| | | | | |
|---|---|---|---|---|
| 2011/0269627 A1* | 11/2011 | Lelas | .................... | C01F 11/185 504/121 |
| 2015/0121979 A1* | 5/2015 | Prasad | .................... | C05D 1/00 71/62 |

FOREIGN PATENT DOCUMENTS

WO   WO-2016040564 A1 *   3/2016   ............... C05D 9/02

* cited by examiner

*Primary Examiner* — John Pak
*Assistant Examiner* — Nathan W Schlientz
(74) *Attorney, Agent, or Firm* — Sherrie Flynn; Coleman & Horowitt LLP

(57) ABSTRACT

Plant supplements that promote plant growth and production and aid in the protection of plants from environmental stress factors such as wind, heat, cold and drought are disclosed. The plant supplements comprise calcium, magnesium and plant-available silica, most typically in a single liquid non-coagulating solution. Optionally, the plant supplements may further comprise iron, nitrogen, willow tree bark extract, humic acid, fulvic acid, aloe vera, trace minerals, electrolytes, beneficial microbes and/or other non-plant food ingredients. Aspects of the present invention also provide methods of formulating and administering plant supplements for promoting plant growth and production, and for protecting plants from environmental stress factors.

19 Claims, No Drawings

PLANT SUPPLEMENTS AND RELATED METHODS

FIELD OF THE INVENTION

The present invention generally relates to the field of plant supplements. Specifically, embodiments of the present invention relate to plant supplements formulated and administered to provide calcium, magnesium and plant-available silica, as well as other key nutrients in a single formulation to promote crop growth and production, and aid the plant in resisting environmental stresses.

DISCUSSION OF THE BACKGROUND

Because plants are generally in a fixed location, they have to be adaptable to the stresses in their environments in order to grow and produce. Stress factors may include temperature, humidity, light intensity, supply of water (or lack thereof), supply of minerals and carbon dioxide. Additionally, such factors as wind, ionizing rays, soil movement and pollutants also affect plant growth, production and propagation. The ability of plants to adapt to varying stress factors may be improved by providing certain nutrients, in appropriate quantities, to the plants. Nutrients that have been found to be beneficial to plants in adapting to stress factors include calcium, magnesium, silica, nitrogen and iron, among others. If such nutrients are not readily available in the soil or air in the plant's environment, fertilizers and plant supplements may be necessary to promote vigorous growth and increase or sustain yield.

Prior to the present invention, known plant supplements included combinations of (1) calcium and magnesium; (2) calcium, magnesium and iron; and (3) calcium, magnesium and zinc, as well as calcium/magnesium with other trace minerals. However, prior to the present invention, no known supplements were available that contain calcium and magnesium along with a plant-available silica in a single liquid suspension because calcium/magnesium products for hydroponics, green house crop production and agricultural growth products have not been able to be blended in a packaged container in a liquid suspension. For convenience and economy, a single formulation that contains silica as well as calcium and magnesium is preferable to separately administering these nutrients.

Additionally, silica in suspension with calcium and magnesium charges and aids in calcium uptake, and helps the plant to endure environmental stress factors (such as those identified above) by bolstering cell walls and aiding in root development. The root, especially the root hair, is the essential organ for the uptake of nutrients. The structure and architecture of the root can alter the rate of nutrient uptake. Therefore, silica is essential for healthy roots and proper nutrient absorption.

Thus, it is desirable to provide plant supplements and methods for administering plant supplements that contain at least calcium, magnesium and silica to promote growth, crop production and help the plants to resist environmental stresses. Optionally, hydrogen, iron, willow tree bark extract, humic acid, fulvic acid, aloe vera, trace minerals, electrolytes and/or microbes, and/or non-plant food ingredients may also be provided in a single liquid suspension.

SUMMARY OF THE INVENTION

Embodiments of the present invention advantageously provide plant supplements and methods of formulating and administering plant supplements that promote plant growth and production, and aid in the protection of plants from environmental stress factors such as wind, heat, cold and drought.

Specifically, the plant supplements of the present invention comprise calcium, magnesium and plant-available silica, most typically in a liquid solution. Optionally, the plant supplements may further comprise iron, nitrogen, willow tree bark extract (salicylic acid), humic acid, fulvic acid, aloe vera, and/or non-plant food ingredients. In some embodiments, the plant supplement of the present invention may additionally, or alternately comprise a humic/fulvic acid complex with trace minerals, electrolytes and microbes.

Methods of administering the plant supplements comprise mixing a quantity of the plant supplement in water and watering plants with the mixture, wherein the plant supplement comprises at least 0.15% by weight of silica; at least 2.00% by weight of calcium; and at least 1.00% by weight of magnesium, of the total weight of the plant supplement. Optionally, the plant supplements may comprise at least 0.10% by weight of iron, at least 1.00% by weight of nitrogen, at least 0.20% by weight of willow tree bark extract, at least 0.20% by weight of humic acid, at least 0.20% by weight of fulvic acid, at least 0.20% by weight of aloe vera, trace minerals, electrolytes, soil born organisms (microbes) and/or non-plant food ingredients.

Thus, embodiments of the present invention advantageously provide calcium, magnesium and plant-available silica as well as other nutrients in a single plant supplement to promote plant growth and production, as well as help plants to resist environmental stress factors by, among other things, bolstering cell walls and aiding in root development.

It is to be understood that both the foregoing general description and the following detailed description are exemplary, but not restrictive, of the invention. A more complete understanding of the embodiments of the nutritional supplements and methods disclosed herein will be afforded to those skilled in the art.

DETAILED DESCRIPTION OF THE PREFERRED EMBODIMENTS

Reference will now be made in detail to the preferred embodiments of the invention. While the invention will be described in conjunction with the preferred embodiments, it will be understood that they are not intended to limit the invention to these embodiments. On the contrary, the invention is intended to cover alternatives, modifications, and equivalents that may be included within the spirit and scope of the invention. Furthermore, in the following detailed description of the present invention, numerous specific details are set forth in order to provide a thorough understanding of the present invention. However, it will readily be apparent to one skilled in the art that the present invention may be practiced without these specific details.

Embodiments of the present invention advantageously provide plant supplements and methods for administering plant supplements that include calcium, magnesium and plant-available silica, most typically in a liquid solution, which protect the plants from environmental stress factors throughout the growth cycle, and also aid in plant growth, production and yield. In addition, embodiments of the present invention may also provide other beneficial nutrients and micronutrients to plants, including but not limited to nitrogen, iron, willow tree bark extract, humic acid, fulvic acid, aloe vera, trace minerals, electrolytes and beneficial soil born organisms.

The nutrient components of the instant invention are typically provided in a non-coagulating liquid suspension. The silica in suspension aids in calcium uptake and helps the plant resist stress factors by bolstering cell walls and aiding in root development.

In aspects of the present invention, the silica comprises at least 0.15% by weight of the total weight of the plant supplement, the calcium comprises at least 2.00% by weight of the total weight of the plant supplement and the magnesium comprises at least 1.00% by weight of the total weight of the plant supplement. In some instances, the plant supplements of the present invention optionally comprise iron. In the instances containing iron, the iron may comprise at least 0.10% by weight of the total weight of the supplement. Alternatively or in addition, the plant supplements may contain nitrogen. In embodiments containing nitrogen, the nitrogen may comprise at least 1.00% by weight of the total weight of the supplement. In further embodiments, the plant supplements may contain at least 0.20% willow tree bark extract by weight, at least 0.20% humic acid by weight, at least 0.20% fulvic acid by weight and/or at least 0.20% aloe vera by weight of the total weight of the supplement. In even further embodiments, the plant supplements may comprise a humic/fulvic acid complex, including trace minerals, electrolytes and microbes.

Most preferably, embodiments of the plant supplement of the present invention may contain between 0.15% and 0.50% by weight of silica, between 2.00% and 8.00% by weight of calcium, and between 1.00% and 4.00% percent by weight of magnesium. Optionally, embodiments of the plant supplement may comprise between 1.00% and 7.00% by weight of nitrogen. Alternately, or in addition, the plant supplements may contain between 0.10% and 0.40% by weight of iron, and between 0.20% and 1.5% by weight of willow tree bark extract. Further, the plant supplements may contain between 0.20% and 1.50% by weight of each of humic acid and/or fulvic acid and/or between 0.20% and 1.50% by weight of aloe vera. In some embodiments, the plant supplements may alternately, or additionally, contain a humic/fulvic acid complex with trace minerals and electrolytes. In further embodiments, humic/fulvic acid complex may also contain beneficial soil born organisms (beneficial bacteria and/or fungi). In embodiments in which the humic/fulvic acid blend comprises beneficial soil born organisms, the blend may comprise a minimum of 40 colony forming units (cfu) per strain of organism in a humic/fulvic blend at 1% solution.

Preferably, the plant supplements may contain 0.23% by weight of silica, 4.61% by weight of calcium and 1.26% by weight of magnesium of the total weight of the supplement. In supplements containing iron, preferably the plant supplement contains 0.18% by weight of iron of the total weight of the supplement. In supplements containing nitrogen, preferably, the supplement contains 3.99% by weight of nitrogen, of the total weight of the plant supplement. In supplements containing willow tree bark extract, preferably the plant supplement contains 0.40% by weight of willow tree bark extract. In supplements containing humic acid, preferably the plant supplement contains 0.50% by weight of humic acid. In supplements containing fulvic acid, preferably the plant supplement contains 0.50% by weight of fulvic acid. In supplements containing aloe vera, preferably the plant supplement contains 0.50% to 1.00% by weight of aloe vera. All percentages shown are percentages of the total weight of the plant supplement.

Embodiments of the present invention may include calcium from one or more calcium compounds (e.g., calcium carbonate, calcium phosphate, calcium gluconate, calcium chloride, calcium nitrate). Most typically, embodiments of the present invention include calcium from calcium nitrate ($Ca(NO_3)_2$), an inorganic compound. Calcium nitrate is a colorless granular solid and may be either an anhydrous compound or a tetrahydrate.

One or more magnesium compounds may be used in embodiments of the invention, which may include one or more of magnesium acetate, magnesium L-threonate, magnesium taurate, magnesium chloride, magnesium lactate, magnesium carbonate, magnesium citrate, magnesium nitrate, etc. Most typically, embodiments of the present invention include magnesium from magnesium acetate. Magnesium acetate ($Mg(C_2H_3O_2)_2$ or in its hydrated form $Mg(CH_3COO)_2 \cdot 4H_2O$) is a magnesium salt of acetic acid. It generally appears as white hygroscopic crystals and is soluble in water.

Silica (Si), derived from silicon dioxide ($SiO_2$), is one of the most abundant of materials and is often used as a flow agent or to absorb water in hygroscopic applications. Silica may be categorized as crystalline, amorphous and synthetic amorphous. Silica is ubiquitous. However, until the present invention, the combination of calcium, magnesium and plant-available silica has not been able to be blended in a liquid suspension and packaged for use because silica generally absorbs water and causes coagulation of fluids. Typical embodiments of the present invention utilize a 25% silicon dioxide gel-like concentrate that is 100% water soluble, eliminating prior problems with coagulation when incorporating silica into a liquid suspension.

Some embodiments of the present invention may include iron derived from iron DTPA, a chelated form of iron that is water soluble, making it accessible to plants. Iron is a micronutrient, which in the ferrous state, may be needed by at least some plants. FeDTPA is often referred to by the name iron chelate. Plants generally require iron in the ferrous state ($Fe^{2+}$). When used to chelate iron, DTPA ensures that the iron is kept in the ferrous state over time so that it can be utilized by plants without expending additional energy to convert it from its ferric state ($Fe^{+3}$).

In further embodiments, the plant supplements may contain willow tree bark extract ($C_7H_6O_3$), a monohydroxybenzoic acid, a type of phenolic acid, and a beta hydroxyl acid. Willow tree bark extract is colorless crystalline organic acid, known more commonly as salicylic acid. Willow tree bark extract (salicylic acid) may have the formula $C_6H_4(OH)COOH$, where the OH group is ortho to the carboxyl group. In this form, it is also known as 2-hydroxybenzoic acid.

In some aspects, the plant supplements may contain humic acid and/or fulvic acid. Humic acid is a major constituent of soil. Both humic and fulvic acids are a family of organic acids. The differences between humic acid and fulvic acid are the carbon and oxygen contents, acidity and color, among other differences.

In some instances, the plant supplements may contain a humic/fulvic acid complex, which, in some further instances may contain a plurality of trace minerals, electrolytes and/or microbes (beneficial fungi and bacteria). Trace minerals may comprise one or more of Aluminum (Al), Antimony (Sb), Arsenic (As), Barium (Ba), Beryllium (Be), Bismuth (Bi), Boron (B), Bromine (Br), Cadmium (Cd), Calcium (Ca), Cerium (Ce), Cesium (Cs), Chlorine (Cl), Chromium (Cr), Cobalt (Co), Copper (Cu), Dysprosium (Dy), Erbium (Er), Europium (Eu), Gadolinium (Gd), Gallium (Ga), Germanium (Ge), Gold (Au), Hafnium (Hf), Holmium (Ho), Indium (In), Iodine (I), Iridium (Ir), Iron (Fe), Krypton (Kr), Lanthanum (La), Lutetium (Lu), Lead (Pb), Lithium (Li), Magnesium (Mg), Manganese (Mn), Mercury (Hg), Molybdenum (Mo), Neodymium (Nd), Nickel (Ni), Niobium (Nb), Osmium (Os), Palladium (Pd), Phosphorus (P), Platinum (Pt), Potassium (K), Praseodymium (Pr), Rhenium (Re), Rhodium (Rh), Rubidium (Rb), Ruthenium (Ru), Samarium (Sm), Scandium (Sc), Selenium (Se), Silicon (Si), Silver (Ag), Sodium (Na), Strontium (Sr), Sulfur (S), Tantalum (Ta), Tellurium (Te), Terbium (Tb), Thallium (Tl), Thorium (Th), Thulium (Tm), Tin (Sn), Titanium (Ti), Tungsten (W), Uranium (U), Vanadium (V), Xenon (Xe), Ytterbium (Yb), Yttrium (Y), Zinc (Zn) and Zirconium (Zr).

Microbes, may include ectomycorrhizae, endomycorrhizae and/or *Trichoderma*, and may also include one or more of *Bacillus Pumilus, Bacillus Mageterium, Bacillus Subtillis, Bacillus Lactis, Bacillus Linchenformis, Bacillus Amyloliquerfaciens, Bacillus Infantis, Bacillus Breve, Bacillus Longum, Bifidobacterium Bifidum, Streptococcus Thermophilus, Lactobacillus Acidophilus, Lactobacillus Rhamnosus, Lactobacillus Salivarius, Lactobacillus Casi, Lactobacillus Lactis,* and *Lactobacillus*, which may be stored in a non-refrigerated complex, and which can withstand environmental stress factors. In addition or alternatively, the humic/fulvic acid complex may contain electrolytes with an alkaline pH. Electrolytes may comprise one of more of sodium ($Na^+$), potassium ($K^+$), calcium ($Ca^{2+}$), magnesium ($Mg^{2+}$), hydrogen phosphate ($HPO_4^{2-}$) and/or hydrogen carbonate ($HCO_3^-$).

The plant supplements of the present invention may optionally contain aloe vera, most typically slow dried inner fillet powder or flake, with short chain polysaccharides. Aloe vera has been shown in some studies to provide medicinal and healing properties, and in the form of a dried inner fillet powder or flake is more bio available for plant nutrient uptake.

It is expressly intended that all ranges broadly recited in this document include all narrower ranges that fall within the broad ranges.

Exemplary Formulations:

The following examples of particular embodiments are given for illustrative purposes only. The examples are not intended to be a limitation on the scope or practice of the invention. Numerous variations of the present invention are possible without departing from the spirit and scope of the invention.

Example 1: Silica 0.20%; Calcium 4.30%; Magnesium 1.5%.

Example 2: Silica 0.18%; Calcium 5.05%; Magnesium 2.15%.

Example 3: Silica 0.23%; Calcium 4.61%; Magnesium 1.00%.

Example 4: Silica 0.35%; Calcium 6.00%; Magnesium 2.87%; Iron 0.25%.

Example 5: Silica 0.20%, Calcium 4.59%, Magnesium 1.25%; Nitrogen 3.99%.

Example 6: Silica 0.45%; Calcium 7.80%; Magnesium 3.78%; Willow tree bark extract 0.40%; aloe vera 0.015%.

Example 7: Silica 0.23%; Calcium 4.60%; Magnesium 1.27%; Iron 0.15%; Humic Acid 0.50%; Fulvic Acid 0.40%.

Example 8: Silica 0.23%, Calcium 4.61%; Magnesium 1.26%; Aloe Vera 1.0%; Humic/Fulvic Acid Complex 1.00%

As indicated above, these are just a few of the formulations of the plant supplements of the present invention and are for illustrative purposes only. The formulations may contain any combination of the nutrients listed, in any percentage within the ranges specified herein.

Exemplary Methods of Administering

Typically, the plant supplements of the present invention should be administered by adding a quantity of the supplement to the plant water supply at the source. Recommended dosages comprise:

2 milliliters (ml) of the plant supplement per gallon of water for seedlings;
6 ml per gallon of water for early seedlings;
8 ml per gallon of water for late vegetation;
10 ml per gallon of water for early flowering;
10 ml per gallon of water for late flowering; and
12 ml per gallon of water for mid-flowering.

The recommended dosages are based on a plant supplement comprising at least 0.15% by weight of silica, at least 2.00% by weight of calcium, and at least 1.00% by weight of magnesium of the total weight of the plant supplement. The plants are then watered according to their normal watering schedule. Optionally, the plant supplements may contain at least 0.10% by weight of iron, at least 1.00% by weight of nitrogen, at least 0.20% by weight of willow tree bark extract, at least 0.20% by weight of humic acid and/or at least 0.20% by weight of fulvic acid, of the total weight of the plant supplement.

Preferably, the supplements administered by the above recommended dosages comprise 0.23% by weight of silica, 4.61% by weight of calcium and 1.26% by weight of magnesium of the total weight of the supplement. In supplements containing iron, preferably the plant supplement contains 0.18% by weight of iron of the total weight of the supplement. In supplements containing nitrogen, preferably, the supplement contains 3.99% by weight of nitrogen, of the total weight of the plant supplement. In supplements containing willow tree bark extract, preferably the plant supplement contains 0.40% by weight of willow tree bark extract of the total weight of the plant supplement. In supplements containing humic and/or fulvic acid, preferably the plant supplement contains 0.50% by weight of each of humic and/or fulvic acid of the total weight of the plant supplement.

What is claimed is:

1. A non-coagulating, aqueous liquid solution plant supplement for promoting plant growth and production, comprising:
   silicon dioxide, wherein the silicon dioxide is amorphous, water soluble, immediately bioavailable and comprises at least 0.15% and up to 4.5% by weight of the total weight of the plant supplement;
   calcium nitrate;
   and magnesium acetate;
   wherein the silicon dioxide, calcium nitrate and magnesium acetate are blended in a packaged container.

2. The plant supplement of claim 1, wherein the silicon dioxide comprises less than 0.50% by weight of the total weight of the plant supplement.

3. The plant supplement of claim 1, wherein the silicon dioxide is 0.23% by weight, the calcium nitrate is 4.61% by weight, and the magnesium acetate is 1.26% per weight, of the total weight of the plant supplement.

4. The plant supplement of claim 1, further comprising iron.

5. The plant supplement of claim 1, further comprising nitrogen.

6. The plant supplement of claim 1, further comprising willow tree bark extract, humic acid and/or fulvic acid.

7. A non-coagulating, aqueous liquid solution for promoting plant growth and production, the solution comprising:

at least 0.15% by weight of silicon dioxide and up to 4.5%, wherein the silicon dioxide is amorphous, immediately bioavailable and water soluble;
at least 2.00% by weight of calcium, wherein the calcium is from calcium nitrate;
at least 1.00% by weight of magnesium, wherein the magnesium is from magnesium acetate;
of the total weight of the liquid solution;
wherein the silicon dioxide, calcium nitrate and magnesium acetate are blended in a packaged container.

8. The liquid solution of claim 7, wherein the silicon dioxide is 0.23% by weight, of the total weight of the liquid solution.

9. The liquid solution of claim 7, wherein the calcium is 4.61% by weight, of the total weight of the liquid solution.

10. The liquid solution of claim 7, wherein the magnesium is 1.26% by weight, of the total weight of the liquid solution.

11. The liquid solution of claim 7, further comprising at least 0.10% by weight of iron, of the total weight of the liquid solution.

12. The liquid solution of claim 7, further comprising at least 1.00% by weight of nitrogen, of the total weight of the liquid solution.

13. A method of administering a non-coagulating, aqueous liquid solution plant supplement, the method comprising:
(i) mixing a quantity of the plant supplement in water, wherein the plant supplement comprises:
at least 0.15% and up to 4.50% by weight of silicon dioxide, wherein the silicon dioxide is amorphous, immediately bioavailable and water soluble;
at least 2.00% by weight of calcium, wherein the calcium is from calcium nitrate;
at least 1.00% by weight of magnesium, wherein the magnesium is from magnesium acetate;
of the total weight of the plant supplement; and
wherein the silicon dioxide, calcium nitrate and magnesium acetate are blended in a packaged container; and
(ii) the non-coagulating, aqueous liquid solution plant supplement plants with mixture.

14. The method of claim 13, wherein the quantity is at least 2 ml per gallon of the water for seedlings and cuttings.

15. The method of claim 13, wherein the quantity is at least 6 ml per gallon of the water for early vegetation.

16. The method of claim 13, wherein the quantity is at least 8 ml per gallon of the water for late vegetation.

17. The method of claim 14, wherein the quantity is at least 10 ml per gallon of the water for early or late flowering.

18. The method of claim 13, wherein the quantity is at least 12 ml per gallon of the water for mid flowering.

19. The method of claim 13, wherein the plant supplement comprises 0.23% by weight of silicon dioxide, 4.61% by weight of calcium nitrate, and 1.26% by weight of magnesium acetate, of the total weight of the plant supplement.

* * * * *